(12) United States Patent
Miyamoto et al.

(10) Patent No.: US 7,824,665 B2
(45) Date of Patent: Nov. 2, 2010

(54) DISINFECTANT GEL FOR HANDS

(75) Inventors: Koji Miyamoto, Tsukuba (JP); Yoshimi Sekine, Tsukuba (JP); Hiroki Fukui, Tsukuba (JP); Kenshiro Shuto, Tsukuba (JP)

(73) Assignee: NOF Corporation, Tokyo (JP)

(*) Notice: Subject to any disclaimer, the term of this patent is extended or adjusted under 35 U.S.C. 154(b) by 868 days.

(21) Appl. No.: 11/533,639

(22) Filed: Sep. 20, 2006

(65) Prior Publication Data

US 2007/0065388 A1    Mar. 22, 2007

(30) Foreign Application Priority Data

Sep. 22, 2005    (JP)    ............................. 2005-274883

(51) Int. Cl.
*A61K 8/81* (2006.01)
*A61K 8/73* (2006.01)
*A01N 25/00* (2006.01)

(52) U.S. Cl. .................. 424/70.13; 424/70.16; 424/405

(58) Field of Classification Search ........................ None
See application file for complete search history.

(56) References Cited

U.S. PATENT DOCUMENTS 5,063,052 A    11/1991    Grollier et al.
5,468,475 A *  11/1995    Shaku et al. ............. 424/70.16
5,795,916 A *  8/1998     Sekine et al. ................ 514/567

FOREIGN PATENT DOCUMENTS

| EP | 0223681 A1 | 5/1987 |
| EP | 0604848 A2 | 7/1994 |
| FR | 2141853 A1 | 1/1973 |
| FR | 2785537 A1 | 5/2000 |
| GB | 2017491 | 10/1979 |
| GB | 1023895 | 3/1996 |
| JP | 04-305504 | 10/1992 |
| JP | 05-255078 | 10/1993 |
| JP | 06-199700 | 7/1994 |
| WO | WO 03-003938 A1 | 1/2003 |

* cited by examiner

*Primary Examiner*—Shanon A Foley
(74) *Attorney, Agent, or Firm*—Sughrue Mion, PLLC

(57) ABSTRACT

The invention provides a quick-drying disinfectant gel for hands that spreads well in rubbing into hands, spreads easily over the hands, forms no scum, and is not sticky before and after drying. The disinfectant gel for hands of the invention contains 0.01 to 2.0 wt % of a maleic anhydride polymer, 0.01 to 5.0 wt % of polysaccharides, 40 to 95 wt % of a lower alcohol, and water, with the total being 100 wt %.

12 Claims, No Drawings

DISINFECTANT GEL FOR HANDS

FIELD OF ART

The present invention relates to disinfectant gel for hands that is used for disinfecting hands in food industry, medical sites, and the like for hygienic management. In particular, the present invention relates to easy-to-use, quick-drying, disinfectant gel for hands that may achieve the desired effect merely by applying to and rubbing into the hands.

BACKGROUND ART

Quick-drying rubbing alcoholic disinfectants have advantages typically in that they may disinfect the hands simply by applying or spraying it to the hands, and require no towel drying. Such rubbing alcohol is widely used as covering the shortcomings of the basin method (dipping method). This type of disinfectant is, however, in the form of an alcoholic liquid preparation, and as such often flows over the palm upon dispensing it into the palm, and also in applying it to and rubbing it into the hands. Further, the flown or spilled alcoholic liquid may contact and deteriorate building parts or instruments JP-4-305504-A proposes a quick-drying rubbing alcoholic disinfectant, wherein the above various disadvantages are overcome by thickening or gelling an alcoholic liquid preparation with a water-soluble polymer, such as carboxyvinyl polymers.

However, the disninfectants containing a carboxyvinyl polymer as a thickener form scum of polymer deposit on the hands after application, and have problems in the feel of use.

In order to improve the feel of use deteriorated with the scum, JP-6-199700-A reports a quick-drying disinfectant gel for hands composed of an alcoholic disinfectant blended with a disinfectious medicament, a carboxyvinyl polymer, and a water-soluble, high molecular cellulose compound.

However, even such a quick-drying disinfectant gel for hands may sometimes form scum, or the moisture may make the gel sticky, so that the desired effect is not fully achieved. In particular, even when the applied disinfectant is dried before airtight surgical gloves are put on, stickiness and sliminess may still be felt in the gloves when sweated.

SUMMARY OF THE INVENTION

It is an object of the present invention to provide a quick-drying disinfectant gel for hands that spreads well in rubbing into hands, spreads easily over the hands, forms no scum, and is not sticky before and after drying.

According to the present invention, there is provided a disinfectant gel for hands comprising 0.01 to 2.0 wt % of a maleic anhydride polymer, 0.01 to 5.0 wt % of polysaccharides, 40 to 95 wt % of a lower alcohol, and water, with the total being 100 wt % (sometimes referred to as the disinfectant of the present invention hereinbelow)

PREFERRED EMBODIMENTS OF THE INVENTION

The present invention will now be explained in detail.

The disinfectant of the present invention contains a maleic anhydride polymer, polysaccharides, a lower alcohol, and water as the indispensable components at a particular ratio, and takes the form of a gel.

The disinfectant of the present invention may optionally contain components other than these indispensable components as will be discussed later However, a carboxyvinyl polymer, which has conventionally been used widely in a disinfectant gel for hands, may impair the scum preventing effect, if contained.

The maleic anhydride polymer may be a homopolymer or a copolymer of maleic anhydride. A copolymer may be, for example, an ethylene-maleic anhydride copolymer or a methylvinyl ether-maleic anhydride copolymer, with the latter being particularly preferred for its availability. A copolymer with free acid form or half-esterified form of maleic anhydride group of maleic anhydride copolymer may also be used, Examples of such a copolymer may include copolmers commercially available from ISP under the trade name GANTREZ AN series, which are about 1:1 copolymers.

The maleic anhydride polymer may be a single kind of polymer or a mixture of two or more kinds.

The weight average molecular weight of the maleic anhydride polymer is not particularly limited, and may usually be 10000 to 3000000, preferably 100000 to 2000000.

The content of the maleic anhydride polymer is 0.01 to 2.0 wt % of the total amount of the disinfectant of the present invention. If the content is less than 0.01 wt %, scum tends to form after application, whereas if the content is more than 2.0 wt %, the disinfectant will become sticky or slimy when rubbed into the hands.

The polysaccharides used in the present invention may include natural polysaccharides and derivatives thereof. Examples of the polysaccharides may include carboxymethyl starch, dialdehyde starch, pullulan, mannan, amylopectin, amylose, dextran, hydroxyethyl dextran, levan, inulin, chitin, chitosan, xyloglucan, alginic acid, arabic gum, guar gum, tragacanth gum, hyarulonic acid, heparin, methylcellulose, ethylcellulose, acetylcellulose, nitrocellulose, carboxymethylcellulose, carboxymethylethylcellulose, hydroxyethylcellulose, hydroxypropylcellulose, ethylhydroxyethylcellulose, and hydroxypropylmethylcellulose. One or a mixture of two or more of these may be used. Among these, water-soluble cellulose compounds, such as methylcellulose, ethylcellulose, hydroxyethylcellulose, hydroxypropylcellulose, carboxymethylcellulose, carboxymethylethylcellulose, and hydroxypropylmethylcellulose are preferred, and hydroxypropylcellulose is particularly preferred for its dispersibility in an alcohol solution as a medium.

The molecular weight of the polysaccharides may preferably be 5000 to 5000000 in weight average molecular weight, more preferably 10000 to 1000000 for good feel of use and handling.

The content of the polysaccharides is 0.01 to 5.0 wt % of the total amount of the disinfectant of the present invention. If the content s less than 0.01 wt % the disinfectant is not given sufficient viscosity, whereas if the content is more than 5.0 wt %, slimy touch in application and stickiness after drying may be increased.

The lower alcohol used in the present invention may be, for example, methanol, ethanol, or isopropanol, and a single kind or a mixture of two or more kinds may be used.

The content of the lower alcohol is 40 to 95 wt %, preferably 50 to 85 wt % of the total amount of the present disinfectant. If the content is less than 40 wt %, sufficient sterilizability is not exhibited, whereas if the content is more than 95 wt %, the disinfectant may be hard to be gelled.

The water used in the present invention is not particularly limited, and purified water is preferred. The content of water is usually 4 to 55 wt %, preferably 10 to 30 wt % of the total amount of the present disinfectant.

The composition of the present disinfectant may be decided so that it is given a suitable viscosity for good spreading in application without flowing from the hands. A preferred viscosity is 100 to 50000 mPa·s at 20° C. if the viscosity is lower than 100 mPa·s, the disinfectant may flow or run off when dispensed into or rubbed into the hands. If the viscosity is over 50000 mPa·s, the disinfectant may not spread well, and the feel of use may be deteriorated.

The disinfectant of the present invention may optionally contain, in addition to the above-mentioned indispensable components, various additives in such an amount as to sum up with the indispensable components to the total of 100 wt %, for improving other effects, as long as the desired effects of the present invention are not impaired.

The additives may include disinfecting agents for further sustaining the sterilizing effect of the disinfectant of the present invention. Examples of the disinfecting agent may include invert soaps such as benzalkonium chloride and benzethonium chloride; biguanide compounds, such as chlorhexidine salts, typically chlorhexidine gluconate; phenol compounds, such as cresol; iodine compounds, such as iodine ions, iodoform, and povidone iodine; and pigment compounuds, such as acrynol. One or a mixture of two or more of these may be used.

A preferred content of the disinfecting agent, if any, may usually be 0.005 to 10 wt % of the total amount of the present disinfectant, for achieving the above-mentioned desired effect.

The additives may also include moisturizer for preventing or inhibiting hand roughening caused by repeated use of the present disinfectant. Examples of the moisturizer may include polyol compounds, such as ethylene glycol, diethylene glycol, triethylene glycol, polyethylene glycol, propylene glycol, dipropylene glycol, polypropylene glycol, poloxamer, 1,3-butylene glycol, 1,4-butylene glycol, pentylene glycol, hexylene glycol, isoprene glycol, ethylhexanediol, isopentyldiol, glycerin, diglycerin, polyglycerin, glyceryl linoleate, sorbitol, xylitol, maltitol, mannitol, and erythritol, sodium hyarulonate, sodium chondroitin sulfate, sodium pyrrolidone carboxylate, sodiumlactate, collagen, elastin, mucin, ceramide, urea, trehalose, and derivatives thereof. One or a mixture of two or more of these may be used.

A preferred content of the moisturizer, if any, may usually be 0.01 to 10 wt % of the total amount of the present disinfectant for achieving the desired effect.

The additives may further include a 2-(meth)acryloyloxyethylphosphorylcholine-containing polymer (sometimes abbreviated as MPC polymer hereinbelow) for giving the present disinfectant a stronger effect of preventing or ameliorating hand roughing than given by the moisturizer.

The MPC polymer is a polymer having a constitutional unit derived from 2-(meth)acryloyloxyethylphosphorylcholine (abbreviated as MPC hereinbelow), and is obtained by radical polymerization of a monomer composition containing MPC.

The MPC may be prepared by a conventional method, such as that disclosed in JP-54-63025-A or JP-58-154591. Specifically, 2-hydroxyethylmethacrylate and a cyclic phosphorus compound are reacted in the presence of a basic catalyst, such as triethylamine, the resulting cyclic phosphorus compound is ring-opened with trimethylamine. and the product is purified by recrystallization.

The MPC polymer may be a copolymer of MPC and another monomer. Examples of such another monomer may include methyl(meth)acrylate, ethyl(meth)acrylate, propyl(meth)acrylate, butyl(meth)acrylate, hexyl(meth)acrylate, 2-ethylhexyl(meth)acrylate, decyl(meth)acrylate, dodecyl(meth)acrylate, tetradecyl(meth)acrylate, hexadecyl(meth)acrylate, octadecyl(meth)acrylate, docosanyl(meth)acrylate, benzyl(meth)acrylate, phenoxyethyl(meth)acrylate, cyclohexyl(meth)acrylate, polypropylene glycol mono(meth)acrylate, polytetramethylene glycol mono(meth)acrylate, polypropylene glycol di(meth)acrylate, polytetramethylene glycol di(meth)acrylate, polypropylene glycol polyethylene glycol mono(meth)acrylate, glycidyl (meth)acrylate, (meth)acryloyloxypropyltrimethoxysilane, styrene, methylstyrene, chloromethylstyrene, methylvinyl ether, butylvinyl ether, vinyl acetate, vinyl propionate, vinyl decanoate, vinyl dodecanoate; vinyl hexadecanoate, vinyl octadecanoate, vinyl docosanoate, 2-hydroxyethyl(meth)acrylate, 2-hydroxybutyl (meth)acrylate, 4-hydroxybutyl(meth)acrylate, (meth)acrylic acid, styrene sulfonic acid, (meth)acrylamide, 2-acrylamide-2-methylpropanesulfonic acid, (meth)acryloyloxyphosphonic acid, aminoethylmethacrylate, dimethylaminoethyl(meth)acrylate, diethylaminoethyl(meth)acrylate, maleic anhydride, glyco-2-hydroxyethylmonomethacrylate (GEMA), 2-hydroxy-3-(meth)acryloxypropyltrimethylammonium chloride, polyethylene glycol mono(meth)acrylate, N-vinyl-2-pyrrolidone, vinyl pyridine, vinyl chloride, vinyliden chloride, ethylene, propylene, isobutylene, and acrylonitrile. Among these, methacrylate monomers are particularly preferred for easy solution polymerization. For preparation of a copolymer, one or a mixture of two or more of these monomers may be used.

A preferred molecular weight of the MPC polymer is usually 5000 to 5000000 in weight average molecular weight.

A preferred content of the MPC polymer, if any, may usually be 0.001 to 10 wt % of the total amount of the present disinfectant for achieving the desired effect.

The additives may also include a pH and viscosity adjusting agent composed of a basic substance for adjusting the pH or viscosity of the disinfectant. Example of the basic substance may include sodium hydroxide, potassium hydroxide, aqueous ammonia, monoethanolamine, diethanolamine, triethanolamine, diisopropanolamine, aminomethylpropanol, triethylamine, tetrahydroxypropylethylenediamine, and mixtures thereof.

The content of the pH and viscosity adjusting agent, if any, may suitable be selected for achieving the desired effect.

The disinfectant of the present invention may further contain, in addition to the additives mentioned above, further additives that are used for ordinary medicine for external use, such as surfactants, dyes, organic acids, inorganic salts, antioxidants, stabilizers, preservatives, chelating agents, flavoring agents, or pigments, as long as the properties of the present invention are not impaired.

Since the present invention has the above compositions in particular, since the particular amounts of maleic anhydride polymer and polysaccharides are blended in a high concentration aqueous solution of a lower alcohol, the present disinfectant has no scumming problem in use, a moderate viscosity for not flowing from the hands, good feel of use, and sufficient disinfecting and quick-drying properties. Thus the present invention is useful as a hand disinfectant for use in food industry and medical sites.

EXAMPLES

The present invention will now be explained in more detail with reference to Examples and Comparative Examples, which do not intend to limit the present invention.

Example 1

0.6 g of a sodium hydroxide aqueous solution (1 mol/L) and 0.2 g of a methylvinyl ether-maleic anhydride copolymer (Gantrez AN-119, manufactured by ISP Japan, molecular weight Mw=216000) were added to 15.1 g of distilled water, stirred at 80° C. until the copolymer was completely dissolved, and allowed to cool to the room temperature.

On the other hand, 5.0 g of isopropanol and 1.5 g of hydroxypropylcellulose were added to 77.6 g of ethanol, and stirred to obtain a homogenous solution. To the resulting ethanol solution, the aqueous solution of the methylvinyl ether-maleic anhydride copolymer prepared above was added, and stirred sufficiently with a homomixer until the entire system became homogenous, to thereby obtain 100 g of a disinfectant gel for hands. The viscosity of the obtained disinfectant was measured at 20° C. using a type B viscometer. The results are shown in Table 1.

Examples 2 to 11

Disinfectant gels for hands of Examples 2 to 11 were prepared in the same way as in Example 1, except that the kinds and amounts of the components were changed as shown in Table 1. The viscosity of the obtained disinfectants was also measured in the same way as in Example 1. The results are shown in Table 1.

the kinds and amounts of the components were changed as shown in Table 2. The viscosity of the obtained disinfectants was also measured in the same way as in Example 1. The results are shown in Table 2.

Comparative Example 8

A disinfectant gel for hands was prepared from the components shown in Table 2. That is, 0.22 g of benzalkonium chloride was dissolved in 78.5 g of ethanol of Japanese Pharmacopoeia grade, 0.2 g of glycerin was added, the mixture was stirred, 0.5 g of hydroxypropylmethylcellulose was added and homogeneously dispersed.

On the other hand, 0.8 g of carboxyvinyl polymer was added to 19.4 g of purified water, and thoroughly stirred to obtain a homogeneous solution. Then 0.38 g of diisopropanolamine was added, and the mixture was thoroughly stirred until a homogeneous gel was obtained. The benzalkonium chloride solution prepared above was added to the gel, and the mixture was thoroughly stirred until the system became homogeneous, to thereby obtain 100 g of a quick-drying disinfectant gel for hands, which was transparent and color-

TABLE 1

| | Component (g) | Example 1 | 2 | 3 | 4 | 5 | 6 | 7 | 8 | 9 | 10 | 11 |
|---|---|---|---|---|---|---|---|---|---|---|---|---|
| Polymer | Methylvinyl ether-maleic anhydride copolymer[1] | 0.2 | 0.2 | 0.2 | 0.2 | 0.2 | 0.2 | 0.2 | 0.2 | 0.2 | 0.2 | 0.2 |
| | Hydroxypropylcellulose[2] | 1.5 | — | 1.5 | 1.5 | 1.5 | 1.5 | — | 1.5 | 1.5 | 1.5 | 1.5 |
| | Dextran[3] | — | 1.5 | — | — | — | — | 1.5 | — | — | — | — |
| Alcohol | Ethanol | 77.6 | 77.6 | 77.6 | 77.6 | 77.6 | 77.6 | 77.6 | 77.6 | 77.6 | 77.6 | 77.6 |
| | Isopropanol | 5.0 | 5.0 | 5.0 | 5.0 | 5.0 | 5.0 | 5.0 | 5.0 | 5.0 | 5.0 | 5.0 |
| Disinfecting agent | Benzalkonium chloride | — | — | — | — | — | 0.25 | 0.25 | 0.25 | 0.25 | 0.25 | — |
| | Chlorhexidine gluconate | — | — | — | — | — | — | — | — | — | — | 0.25 |
| Basic substance | Sodium hydroxide (1 mol/L) | 0.6 | 0.6 | — | 0.6 | 0.6 | 0.6 | 0.6 | — | 0.6 | 0.6 | 0.6 |
| | Diisopropanolamine | — | — | 0.5 | — | — | — | — | 0.5 | — | — | — |
| Moisturizer Other | Glycerin | — | — | — | 1.0 | — | — | — | — | 1.0 | — | — |
| | Isopropyl myristate | — | — | — | — | 0.5 | — | — | — | — | 0.5 | 0.5 |
| Additives | MPC-BMA copolymer[4] | — | — | — | — | 0.4 | — | — | — | — | 0.4 | 0.4 |
| | Water | 15.10 | 15.10 | 15.20 | 14.10 | 14.20 | 14.85 | 14.85 | 14.95 | 13.85 | 13.95 | 13.95 |
| | Total | 100.0 | 100.0 | 100.0 | 100.0 | 10.0 | 100.0 | 100.0 | 100.0 | 100.0 | 100.0 | 100.0 |
| | Viscosity (mPa·s) | 1800 | 700 | 2500 | 1800 | 1600 | 1800 | 800 | 2400 | 1700 | 1700 | 1800 |

[1]Gantrez AN-119, manufactured by ISP Japan, Molecular weight Mw = 216,000
[2]NISSO HPC-H, manufactured by NIPPON SODA CO., LTD., 1,000 to 4,000 mPa·s (2% aqueous solution, type B viscometer, at 20° C.)
[3]Manufactured by WAKO PURE CHEMICALS INDUSTRIES, LTD., molecular weight Mw = 60,000 to 90,000
[4]Lipidure-PMB (copolymer of MPC and butylmethacrylate (5% aqueous solution of MPC/BMA = 8/2 (mol/mol)), manufactured by NOF Corporation, 6.0 to 60.0 mm$^2$/s (Cannon-Fenske viscometer, at 40° C.)

Comparative Examples 1 to 7

Disinfectants for hands of Comparative Example 1 to 7 were prepared in the same way as in Example 1, except that less. The viscosity of the obtained disinfectant was measured in the same way as in Example 1. The results are shown in Table 2.

TABLE 2

| | Component (g) | Comparative Example 1 | 2 | 3 | 4 | 5 | 6 | 7 | 8 |
|---|---|---|---|---|---|---|---|---|---|
| Polymer | Methylvinyl ether-maleic anhydride copolymer[1] | — | 0.005 | 3.0 | 0.2 | 0.2 | 0.2 | 0.2 | — |
| | Carboxyvinyl polymer[2] | — | — | — | — | — | — | — | 0.8 |
| | Hydroxypropylcellulose[3] | 1.5 | 1.5 | 1.5 | — | 0.005 | 6.0 | 1.5 | — |
| | Hydroxypropylmethylcellulose[4] | — | — | — | — | — | — | — | 0.5 |
| Alcohol | Ethanol | 77.6 | 77.6 | 77.6 | 77.6 | 77.6 | 77.6 | 35.0 | 78.5 |
| | Isopropanol | 5.0 | 5.0 | 5.0 | 5.0 | 5.0 | 5.0 | — | — |
| Disinfecting | Benzalkonium chloride | — | — | — | — | — | — | — | 0.22 |

TABLE 2-continued

|  | Component (g) | Comparative Example | | | | | | | |
|---|---|---|---|---|---|---|---|---|---|
|  |  | 1 | 2 | 3 | 4 | 5 | 6 | 7 | 8 |
| agent |  |  |  |  |  |  |  |  |  |
| Basic | Sodium hydroxide (1 mol/L) | 0.6 | 0.6 | 0.6 | 0.6 | 0.6 | 0.6 | 0.6 | — |
| substance | Diisopropanolamine | — | — | — | — | — | — | — | 0.38 |
| Moisturizer | Glycerin | — | — | — | — | — | — | — | 0.2 |
|  | Water | 15.30 | 15.30 | 12.30 | 16.60 | 16.60 | 10.60 | 62.70 | 19.40 |
|  | Total | 100.0 | 100.0 | 100.0 | 100.0 | 100.0 | 100.0 | 100.0 | 100.0 |
|  | Viscosity (mPa·s) | 1100 | 1300 | 2100 | 5 | 5 | 105200 | 2200 | 20000 |

[1] Gantrez AN-119, manufactured by ISP Japan, Molecular weight Mw = 216,000
[2] Carbopol 981, manufactured by NIKKO CHEMICALS, CO., LTD., 4,000 to 7,500 mPa·s (0.2% aqueous solution, at 20° C.)
[3] NISSO HPC-H, manufactured by NIPPON SODA CO., LTD., 1,000 to 4,000 mPa·s (2% aqueous solution, type B viscometer, at 20° C.)
[3] METOLOSE 60SH-4000, manufactured by SHINETSU CHEMICAL CO., LTD., 3,500 to 5,600 mPa·s (2% aqueous solution, at 20° C.)

Test Example 1

Evaluation of Feel of Use

Using twenty male and female panels, the feel of use of the disinfectants prepared in Examples 1 to 11 and Comparative Examples 1 to 8 were evaluated in respect of the following items. The disinfectants of Comparative Examples 4 and 5 were excluded from the test, since these disinfectants were too low in viscosity to give gel samples, and could not be evaluated in the same way as for the other samples. The average point for each of the following test items (1) to (4) was taken as the result of the evaluation, and the test was passed at the average point of 4.0 or higher, and failed at the average point of less than 4.0. The results are shown in Table 3.

(1) Slimy feel in application; 5 points: not slimy; 4 points: little slimy; 3 points: slightly slimy; 2 points: slimy; 1 point: very slimy.
(2) Sticky feel after drying; 5 points: not sticky; 4 points: little sticky; 3 points: slightly sticky; 2 points: sticky; 1 point: very sticky.
(3) Scum after drying; 5 points: no scum; 4 points: little scum; 3 points: some scum; 2 points: much scum; 1 point: a lot of scum.
(4) Sticky feel 30 minutes after wearing surgical gloves following application of disinfectant; 5 points: not sticky; 4 points: little sticky; 3points: slightly sticky; 2 points: sticky; 1 point: very sticky.
(5) Time required for drying; A: moderate (20 to 30 seconds); B: slightly quick (not less than 10 seconds and less than 20 seconds), slightly slow (not less than 30 seconds and less than 40 seconds); C: quick (less than 10 seconds), slow (not less than 40 seconds).

TABLE 3

|  | Quick-drying property | Slimy feel in application | Stickyfeel after drying | Scum after drying | Stickyfeel in gloves |
|---|---|---|---|---|---|
| Ex. 1 | A | 4.5 | 4.5 | 4.7 | 4.7 |
| Ex. 2 | A | 4.6 | 4.1 | 4.2 | 4.2 |
| Ex. 3 | A | 4.2 | 4.2 | 4.6 | 4.4 |
| Ex. 4 | A | 4.2 | 4.2 | 4.7 | 4.4 |
| Ex. 5 | A | 4.3 | 4.4 | 4.5 | 4.3 |
| Ex. 6 | A | 4.5 | 4.5 | 4.6 | 4.8 |
| Ex. 7 | A | 4.7 | 4.1 | 4.6 | 4.3 |
| Ex. 8 | A | 4.4 | 4.5 | 4.3 | 4.4 |
| Ex. 9 | A | 4.2 | 4.2 | 4.6 | 4.3 |
| Ex. 10 | A | 4.3 | 4.3 | 4.5 | 4.3 |

TABLE 3-continued

|  | Quick-drying property | Slimy feel in application | Stickyfeel after drying | Scum after drying | Stickyfeel in gloves |
|---|---|---|---|---|---|
| Ex. 11 | A | 4.1 | 4.4 | 4.2 | 4.4 |
| Comp. Ex. 1 | A | 4.3 | 4.3 | 1.5 | 4.2 |
| Comp. Ex. 2 | A | 4.4 | 4.3 | 2.2 | 4.2 |
| Comp. Ex. 3 | C | 1.3 | 1.4 | 4.2 | 1.2 |
| Comp. Ex. 6 | C | 1.7 | 2.2 | 1.6 | 0.9 |
| Comp. Ex. 7 | C | 1.3 | 2.4 | 4.6 | 2.7 |
| Comp. Ex. 8 | B | 2.7 | 2.5 | 2.3 | 1.5 |

Test Example 2

Evaluation of Sterilizability

Using ten male and female panels, the sterilizability and its persistence of the disinfectants prepared in Examples 5 and 10 and Comparative Examples 1 to 8 were evaluated.

For determining the initial cell count before the experiment, each panel stamped his/her hand on a palm stamp medium (manufactured by NIKKEN BIO MEDICAL LABORATORY). Then each panel took 1 g of the disinfectant and rubbed it into his/her hands for 20 seconds. Immediately after and 2 hours after the disinfection, each panel stamped his/her hand on a palm stamp medium again. After the experiment, the stamped media were incubated in an incubator at 37° C. for 24 hours, and the number of colonies on the media were counted. The sterilizability was represented by the percentage of the number of bacterial colonies immediately after the sterilization to the number before the experiment. The persistency of the sterilizability was represented by the percentage of the number of colonies 2 hours after the sterilization to the number before the experiment. The effect was evaluated by the ratio of decrease in cell count, i.e., the ratio of over 90% was indicated as A, 50 to 89% as B, 1 to 49% as C, and 0% or lower as D. The results are shown in Table 4.

Test Example 3

Evaluation of Effect of Preventing Skin Roughening

Using ten male and female panels, effects of the disinfectants prepared in Examples 5 and 10 and Comparative Examples 1 to 8 on hand skin were determined.

Each panel took 1 g of the disinfectant and rubbed it into his/her hands for 20 seconds. This operation was repeated 5 times a day at 2-hour intervals for consecutive 2 weeks, and then the state of the skin surface was observed using a videomicroscope. The state of roughening of hand skin were evaluated in four levels, i.e., 4 points for no change, 3 points for slightly roughened, 2 points for roughened, and 1 point for apparently roughened. The test was passed at the average point of 3.0 or higher, and failed at the average point of less than 3.0.

TABLE 4

|  | Sterilizability | Persistency of sterilizability | Preventive effect on skin roughening |
|---|---|---|---|
| Example 5 | A | D | 3.9 |
| Example 10 | A | A | 3.8 |
| Comp. Ex. 1 | A | D | 1.4 |
| Comp. Ex. 2 | A | D | 1.7 |
| Comp. Ex. 3 | A | D | 1.5 |
| Comp. Ex. 4 | A | D | 1.5 |
| Comp. Ex. 5 | A | D | 1.6 |
| Comp. Ex. 6 | A | D | 1.8 |
| Comp. Ex. 7 | C | D | 1.8 |
| Comp. Ex. 8 | A | A | 1.2 |

From Tables 1 to 3, it is clarified that the hand disinfectant of the present invention has a moderate viscosity so as not to flow from the hand in use, excellent quick-drying property, no slimy feel in application and no sticky feel after drying, and forms no scum after drying. From Table 4, it is understood that the hand disinfectant of the present invention has both sufficient sterilizability and preventive effect on skin roughening of hands.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to interpreted in a limiting sense. The present invention is limited only by the scope of the following claims.

What is claimed is:

1. A disinfectant gel for hands comprising 0.01 to 2.0 wt % of a maleic anhydride polymer, 0.01 to 5.0 wt % of polysaccharides, 40 to 95 wt % of a lower alcohol, 0.001 to 10 wt % of a 2-(meth)acryloyloxyethylphosphorylcholine-containing polymer, and 4 to 55 wt % of water, with the total being 100 wt %.

2. The disinfectant gel according to claim 1, wherein said maleic anhydride polymer is a methylvinyl ether-maleic anhydride copolymer.

3. The disinfectant gel according to claim 1, wherein said polysaccharides are water-soluble cellulose polymers.

4. The disinfectant gel according to claim 1, wherein said polysaccharides are selected from the group consisting of carboxymethyl starch, dialdehyde starch, pullulan, mannan, amylopectin, amylose, dextran, hydroxyethyl dextran, levan, inulin, chitin, chitosan, xyloglucan, alginic acid, arabic gum, guar gum, tragacanth gum, hyarulonic acid, heparin, methylcellulose, ethylcellulose, acetylcellulose, nitrocellulose, carboxymethylcellulose, carboxymethylethylcellulose, hydroxyethylcellulose, hydroxypropylcellulose, ethylhydroxyethylcellulose, hydroxypropylmethylcellulose, and mixtures thereof.

5. The disinfectant gel according to claim 1, wherein said lower alcohol is selected from the group consisting of methanol, ethanol, isopropanol, and mixtures thereof.

6. The disinfectant gel according to claim 1, wherein said gel has a viscosity of 100 to 50000 mPa·s at 20° C.

7. The disinfectant gel according to claim 1, further comprising an additive selected from the group consisting of a pH and viscosity adjusting agent, a disinfecting agent, a moisturizer, and mixtures thereof.

8. The disinfectant gel according to claim 7, wherein said pH and viscosity adjusting agent is selected from the group consisting of sodium hydroxide, potassium hydroxide, aqueous ammonia, monoethanolamine, diethanolamine, triethanolamine, diisopropanolarnine, aminomethylpropanol, triethylamine, tetrahydroxypropyl ethylenediamine, and mixtures thereof.

9. The disinfectant gel according to claim 7, wherein said disinfecting agent is selected from the group consisting of benzalkonium chloride, benzethonium chloride, chlorhexidine gluconate, cresol, iodine ions, iodoform, povidone iodine, acrynol, and mixtures thereof, and contained in an amount of 0.005 to 10 wt % of the total amount of the disinfectant gel.

10. The disinfectant gel according to claim 7, wherein said moisturizer is selected from the group consisting of polyol compounds, including ethylene glycol, diethylene glycol, triethylene glycol, polyethylene glycol, propylene glycol, dipropylene glycol, polypropylene glycol, poloxamer, 1,3-butylene glycol, 1,4-butylene glycol, pentylene glycol, hexylene glycol, isoprene glycol, ethylhexanediol, isopentyldiol, glycerin, diglycerin, polyglycerin, glyceryl linoleate, sorbitol, xylitol, maltitol, mannitol, and erythritol; sodium hyarulonate, sodium chondroitin sulfate, sodium pyrrolidone carboxylate, sodium lactate, collagen, elastin, mucin, ceramide, urea, trehalose, derivatives thereof, and mixtures thereof, and is contained in an amount of 0.01 to 10 wt % of the total amount of the disinfectant.

11. The disinfectant gel according to claim 1 further comprising an additive selected from the group consisting of surfactants, dyes, organic acids, inorganic salts, antioxidants, stabilizers, preservatives, chelating agents, flavoring agents, pigments, and mixtures thereof.

12. The disinfectant gel according to claim 1, wherein the content of said lower alcohol is 50 to 85 wt % of the total amount of the disinfectant gel.

* * * * *